United States Patent [19]

Esanu

[11] Patent Number: 4,735,950
[45] Date of Patent: Apr. 5, 1988

[54] FURO-(3,4-C)-PYRIDINE DERIVATIVES AND THERAPEUTIC COMPOSITION CONTAINING THE SAME

[75] Inventor: André Esanu, Paris, France

[73] Assignee: Societe de Conseils de Recherches et d'Applications Scientifiques (S.C.R.A.S), Paris, France

[21] Appl. No.: 32,947

[22] Filed: Mar. 30, 1987

Related U.S. Application Data

[63] Continuation of Ser. No. 839,880, Mar. 14, 1986, abandoned, which is a continuation of Ser. No. 593,700, Mar. 26, 1984, Pat. No. 4,581,363.

[30] Foreign Application Priority Data

Apr. 5, 1983 [GB] United Kingdom ............... 8309165
Oct. 18, 1983 [GB] United Kingdom ............... 8327815

[51] Int. Cl.$^4$ .................. A61K 31/44; C07D 491/048
[52] U.S. Cl. ....................................... 514/302; 546/116
[58] Field of Search ........................ 546/116; 514/302

[56] References Cited

U.S. PATENT DOCUMENTS 4,581,363 4/1986 Esanu ................... 546/116

FOREIGN PATENT DOCUMENTS 2092586 8/1982 United Kingdom .

Primary Examiner—Henry R. Jiles
Assistant Examiner—Bernard I. Dentz
Attorney, Agent, or Firm—Lucas & Just

[57] ABSTRACT

This invention relates to 1,3-dihydro-6-methyl-7-hydroxy-furo-(3,4-c)-pyridine derivatives of the general formula I

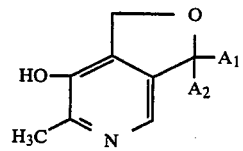

wherein each of $A_1$ and $A_2$ independently represents various hydrocarbon groups and therapeutically acceptable addition salts thereof; to a process for the preparation of the same comprising oxidizing the secondary alcohol $\alpha^4$, 3-o-isopropylidene-1-methyl-5-(1-hydroxy-1-$A_1$)-methyl pyridine by any usual technique, reacting the resultant ketone with a compound of the general formula $XA_2$ wherein X stands for Br or I in the presence of magnesium in diethyl ether at the boil and treating the resultant tertiary alcohol with an acidic agent to provoke breaking of the isopropylidene ring and 3,4-cyclisation; and to pharmaceutical compositions containing these derivatives useful for example in diuresis.

3 Claims, No Drawings

FURO-(3,4-C)-PYRIDINE DERIVATIVES AND THERAPEUTIC COMPOSITION CONTAINING THE SAME

This a continuation of application Ser. No. 839,880, filed Mar. 14, 1986, now abandoned, which in turn is a continuation of application Ser. No. 593,700, filed Mar. 26, 1984, which issued as U.S. Pat. No. 4,581,363, on Apr. 8, 1986.

The invention relates to furo-(3,4-c)-pyridine derivatives, to a process for their preparation and to pharmaceutical compositions containing them.

The invention provides 1,3-dihydro-6-methyl-7-hydroxy-furo-(3,4-c)-pyridine derivatives of the general formula I (and their therapeutically acceptable addition salts):

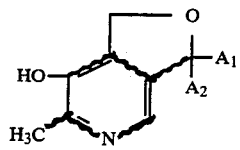

wherein each of $A_1$ and $A_2$ independently represents a straight chain saturated or unsaturated hydrocarbon group having from 1 to 5 carbon atoms, a heterocyclic group having up to 6 ring atoms, a carbomonocyclic group, a phenylalkyl group or a phenylalkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms.

The compounds according to the invention are of interest for their therapeutical activity, principally in the fields of diuresis, the lowering of blood pressure and kidney protection, and as anti-histaminic agents.

The invention further provides a process for the preparation of 1,3-dihydro-6-methyl-7-hydroxy-furo-(3,4-c)-pyridine derivatives of the general formula I as above defined, the process comprising (i) oxidizing the secondary alcohol $\alpha^4$, 3-o-isopropylidene-1-methyl-5-(1-hydroxy-1-$A_1$)-methyl pyridine of the formula:

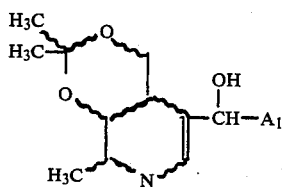

by any usual technique, such as manganese dioxide, for instance, which leads to a ketone, (ii) reacting the resultant ketone with a compound of the general formula $XA_2$ wherein X stands for Br or I and $A_2$ has the meaning given above, in the presence of magnesium in diethyl ether at the boil and (iii) treating the resultant tertiary alcohol with an acidic agent to provoke breaking of the isopropylidene ring and 3,4 cyclisation. The starting secondary alcohol is obtained as described in our previous U.S. Pat. No. 4,383,998.

The process according to the invention is illustrated by the following reaction scheme:

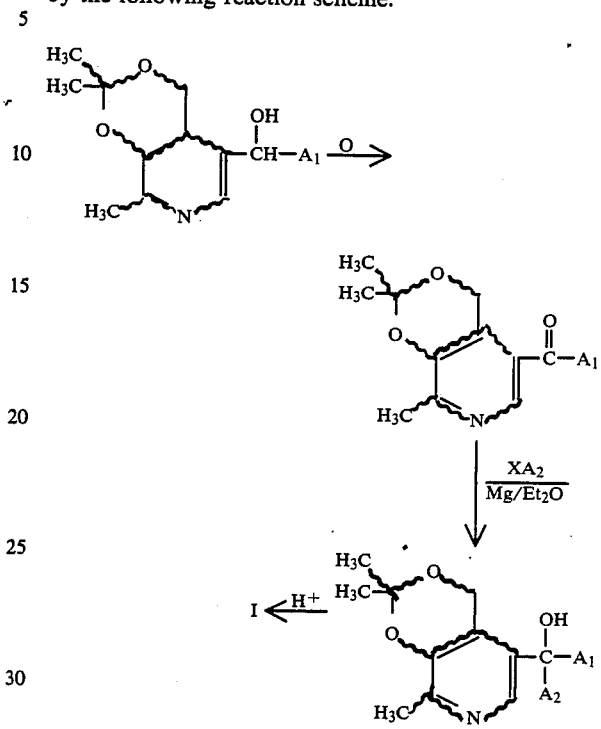

The invention also provides pharmaceutical compositions comprising a furo-(3,4-c)-pyridine derivative of the general formula I as herein defined in admixture with a pharmaceutically acceptable diluent or carrier.

The invention is illustrated by the following examples.

EXAMPLE 1

1,3-dihydro-3,3,6-trimethyl-7-hydroxy-furo-(3,4-c)-pyridine

Into a 3-liter reactor fitted with stirring, warming and cooling means, previously submitted to a nitrogen circulation, were poured 3.47 g (0.143 mol) of magnesium. Slowly, under stirring, there was then added 20.3 g (0.143 mol) of methyl iodide dissolved in 400 ml of distilled diethyl ether. The mixture was refluxed for 2 to 3 hours, then cooled to 10°–15° C. and 22.8 g (0.11 mol of $\alpha^4$, 3-o-isopropylidene pyridoxal dissolved in 600 ml of distilled diethyl ether were slowly added. The mixture was stirred for 12 hours at room temperature, and then the diethyl ether was evaporated off under reduced pressure (end of preparation of starting secondary alcohol). 450 ml of dry methylene dichloride with 30.5 g (0.142 mol) of pyridinium chlorochromate and 2.35 g (0.0285 mol) of pure and dry sodium acetate were poured all at once into the reactor and the mixture was stirred for 2 hours at room temperature, and then for some minutes, after addition of 200 ml of dry diethyl ether. After elimination of insoluble matter, the organic phase was filtered and evaporated to dryness, leading to an oily product (end of step (ii)). This product was dissolved in 400 ml of diethyl ether and treated under stirring for 12 hours at room temperature with a mixture obtained by refluxing for 2 hours 400 ml of diethyl ether, 20 g (0.14 mol) of methyl iodide and 3.45 g (0.14 mol) of magnesium. The diethyl ether was evaporated off under reduced pressure; after cooling, there were added 0.5 l of chloroform and, dropwise, under stirring, 150 ml of 2N hydrochloric acid. Stirring was maintained for 2 hours, the mixture was decanted, the precipitate washed with water, dried on anhydrous sodium sulphate, redissolved in diethyl ether, recrystallized, washed and dried (end of step (iii)). The compound thus obtained was then treated with 100 ml of concentrated hydrochloric acid at room temperature, under stirring for 12 hours. The precipitate obtained was treated twice by ethanol and recrystallized from acetone. Yield 15.9 g (67%) of a pale yellow product melting at 247° C. (Tottoli), elemental analysis of which showed good correspondence with the formula $C_{10}H_{13}NO_2HCl$. The product exhibited good solubility in water at room temperature.

EXAMPLE 2

1,3-dihydro-3-(n-pentyl)-3,6-dimethyl-7-hydroxy-furo-(3,4-c)-pyridine

This compound was obtained as described in example 1 but replacing the methyl iodide by n-pentyl bromide at step (iii). Yield: 72% of a product melting at 222° C. (Tottoli), elemental analysis of which showed good correspondence with the formula $C_{14}H_{21}NO_2.HCl$. The compound exhibited very good solubility in water at room temperature.

EXAMPLE 3

1,3-dihydro-3-phenyl-3,6-dimethyl-7-hydroxy-furo-(3,4-c)-pyridine

This compound was obtained as described in example 1 but replacing the methyl iodide by phenyl bromide in step (i). Yield: 69% of a cream-white product melting at 245° C. (Tottoli), elemental analysis of which showed good correspondence with the formula $C_{15}H_{15}NO_2$. The compound was insoluble in water at room temperature.

EXAMPLE 4

1,3-dihydro-3-(p-chlorophenyl)-3,6-dimethyl-7-hydroxy-furo-(3,4-c)-pyridine

This compound was obtained as described in example 1, but using p-chlorophenyl bromide instead of methyl iodide in step (i). Yield: 63% of a white crystalline powder melting at 228° C. (Tottoli), elemental analysis of which showed good correspondence with the formula $C_{15}H_{14}ClNO_2.HCl$. The compound was insoluble in water at room temperature.

EXAMPLE 5

1,3-dihydro-3-(p-fluorophenyl)-3,6-dimethyl-7-hydroxy-furo-(3,4-c)-pyridine

The compound was obtained as described in example 1, but using p-fluorophenyl bromide instead of methyl iodide in step (i). Yield: 71% of a white crystalline powder melting at 238° C. (Tottoli), elemental analysis of which showed good correspondence with the formula $C_{15}H_{14}FNO_2$. The compound was insoluble in water at room temperature, but soluble in 0.1N HCl.

EXAMPLE 6

1,3-dihydro-3-(α-thienyl)-3,6-dimethyl-7-hydroxy-furo-(3,4-c)-pyridine

This compound was obtained as described in example 2, but using α-thienyl chloride instead of n-pentyl bromide. Yield 74% of a beige product melting at 198° C. (Tottoli), elemental analysis of which showed good correspondence with the formula $C_{13}H_{13}NO_2S.HCl$. The compound was soluble in water.

EXAMPLE 7

1,3-dihydro-3-[2-(3,4,5-trimethoxyphenyl)-ethyl]-3,6-dimethyl-7-hydroxy-furo-(3,4-c)-pyridine This compound was obtained as described in example 1, but replacing the methyl iodide by 1-chloro-2-(3,4,5-trimethoxyphenyl) ethane, in step (i). Yield: 83% of a white product melting at 219° C. (Tottoli), elemental analysis of which showed good correspondence with the formula $C_{20}H_{25}NO_5HCl$. The compound was soluble in water at room temperature.

EXAMPLE 8

1,3-dihydro-3-ethyl-3-(n-propyl)-6-methyl-7-hydroxy-furo-(3,4-c)-pyridine

This compound was obtained as described in example 1, but replacing the methyl iodide by n-propyl bromide in step (i) and by ethyl iodide in step (iii). Yield: 71% of a white crystalline product melting at 212° C. (Tottoli), elemental analysis of which showed good correspondence with the formula $C_{13}H_{19}NO_2.HCl$. The compound was insoluble in water at room temperature.

EXAMPLE 9

1,3-dihydro-3-ethyl-3-(n-butyl)-6-methyl-7-hydroxy-furo-(3,4-c)-pyridine

This compound was obtained as described in example 8, but replacing the n-propylbromide by n-butyl bromide. Yield: 67% of a white crystalline product melting at 238° C. (Tottoli), elemental analysis of which showed good correspondence with the formula $C_{14}H_{21}NO_2.HCl$. The compound was insoluble in water at room temperature.

EXAMPLE 10

1,3-dihydro-3-ethyl-3-phenyl-6-methyl-7-hydroxy-furo-(3,4-c)-pyridine

This compound was prepared as described in example 8, but replacing the n-propyl bromide by phenyl bromide. Yield: 66% of a white crystalline product melting at 234° C. (Tottoli), elemental analysis of which showed good correspondence with the formula $C_{16}H_{17}NO_2$. The compound was insoluble in water at room temperature.

EXAMPLE 11

1,3-dihydro-3-ethyl-3-(p-chlorophenyl)-6-methyl-7-hydroxy-furo-(3,4-c)-pyridine

This compound was obtained as described in example 8, but replacing the n-propyl bromide by p-chlorophenyl bromide. Yield: 77% of a cream-white product melting at 215° C. (Tottoli), elemental analysis of which showed good correspondence with the formula $C_{16}H_{16}ClNO_2$. The compound was insoluble in water at room temperature.

EXAMPLE 12

1,3-dihydro-3-ethyl-3-m-trifluoromethyl phenyl-6-methyl-7-hydroxy-furo-(3,4-c)-pyridine This compound was prepared as described in example 8, but replacing the n-propyl bromide by m-trifluoromethyl phenyl bromide. Yield: 69% of a white crystalline product melting at 207°–208° C. (Tottoli), elemental analysis of which showed good correspondence with the formula $C_{16}H_{16}F_3NO_2$. The compound was insoluble in water at room temperature, but soluble in 0.1N HCl.

EXAMPLE 13

1,3-dihydro-3-ethyl-3-(α-furyl)-6-methyl-7-hydroxy-furo-(3,4-c)-pyridine

This compound was obtained as described in example 8, but replacing the n-propyl bromide by α-furyl bromide. Yield: 73% of a pink product melting at 192° C. (Tottoli) with decomposition, elemental analysis of which showed good correspondence with the formula $C_{14}H_{15}NO_3.HCl$. The compound was insoluble in water at room temperature.

EXAMPLE 14

1,3-dihydro-3-vinyl-3-(p-methylthio-phenyl)-6-methyl-7-hydroxy-furo-(3,4-c)-pyridine This compound was obtained as described in example 1 but replacing the methyl iodide by p-methylthio-phenyl bromide in step (i) and by vinyl bromide in step (iii). Yield: 63% of a cream white crystalline product melting at 200° C. (Tottoli), elemental analysis of which showed good correspondence with the formula $C_{17}H_{17}NO_2S.HCl$. The compound was insoluble in water at room temperature but soluble in dimethylsulphoxide.

EXAMPLE 15

1,3-dihydro-3-propyl-3-p-chlorophenyl-6-methyl-7-hydroxy-furo-(3,4-c)-pyridine This compound was obtained as described in example 1 but replacing the methyl iodide by p-chlorophenyl bromide in step (i) and by propyl iodide in step (iii). Yield: 61% of a white crystalline product melting with decomposition at 188°–190° C. (Tottoli), elemental analysis of which showed good correspondence with the formula $C_{17}H_{18}ClNO_2$. The compound was insoluble in water at room temperature but soluble in 0.1N HCl.

EXAMPLE 16

1,3-dihydro-3-dimethylaminopropyl-3-p-chlorophenyl-6-methyl-7-hydroxy-furo-(3,4-c)-pyridine This compound was prepared as described in example 15 but replacing the propyl iodide by dimethylaminopropyl bromide. Yield: 56% of a white crystalline product melting at 212° C. (Tottoli), elemental analysis of which showed good correspondence with the formula $C_{19}H_{23}N_2O_2Cl$. The compound was insoluble in water at room temperature but soluble in dimethylsulphoxide.

EXAMPLE 17

1,3-dihydro-3,3-diphenyl-6-methyl-7-hydroxy-furo-(3,4-c)-pyridine

This compound was obtained as described in example 1 but replacing the methyl iodide by phenyl bromide in both steps (i) and (iii). Yield: 66% of a white crystalline powder melting at 260° C. (Tottoli) with decomposition, elemental analysis of which showed good correspondence with the formula $C_{20}H_{17}NO_2.HCl$. The compound was insoluble in water at room temperature.

EXAMPLE 18

1,3-dihydro-3-phenyl-3-(p-toluyl)-6-methyl-7-hydroxy-furo-(3,4-c)-pyridine

This compound was obtained as described in example 17 but replacing, in step (i), the phenyl bromide by p-toluyl bromide. Yield: 73% of a white crystalline product melting at 253° C. (Tottoli) with decomposition, elemental analysis of which showed good correspondence with the formula $C_{21}H_{19}NO_2.HCl$. The compound was insoluble in water at room temperature.

EXAMPLE 19

1,3-dihydro-3-phenyl-3-(p-fluorophenyl)-6-methyl-7-hydroxy-furo-(3,4-c)-pyridine This compound was prepared as described in example 17 using, in step (i), p-fluorophenyl bromide instead of phenyl bromide. Yield: 74% of a white crystalline product melting at 259° C. (Tottoli), elemental analysis of which showed good correspondence with the formula $C_{20}H_{16}FNO_2.HCl$. The compound was insoluble in water at room temperature.

EXAMPLE 20

1,3-dihydro-3-(p-trifluoromethylphenyl)-3-phenyl-6-methyl-7-hydroxy-furo-(3,4-c)-pyridine This compound was obtained as described in example 17 but replacing the phenyl bromide by p-trifluoromethylphenyl bromide in step (i). Yield: 71% of a white crystalline product melting at 248° C. with decomposition, elemental analysis of which showed good correspondence with the formula $C_{21}H_{16}F_3NO_2.HCl$. The compound was insoluble in water at room temperature.

EXAMPLE 21

1,3-dihydro-3-(p-ethoxyphenyl)-3-phenyl-6-methyl-7-hydroxy-furo-(3,4-c)-pyridine This compound was obtained as described in example 17 but replacing the phenyl bromide by p-ethoxyphenyl bromide in step (i). Yield: 58% of a white product melting at 230° C. (Tottoli), elemental analysis of which showed good correspondence with the formula $C_{22}H_{21}NO_3.HCl$. The compound was insoluble in water at room temperature.

EXAMPLE 22

1,3-dihydro-3-(p-diethylaminomethoxyphenyl)-3-phenyl-6-methyl-7-hydroxy-furo-(3,4-c)-pyridine This compound was obtained as described in example 16 but replacing, in step (iii), the phenyl bromide by p-diethylaminomethoxyphenyl bromide. Yield: B 56% of a beige powder melting at 202° C. (Tottoli), elemental analysis of which showed good correspondence with the formula $C_{25}H_{28}N_2O_3$. The compound was insoluble in water at room temperature.

EXAMPLE 23

1,3-dihydro-3-{p-[N-(α-methoxypyrrolidinyl)]-phenyl}-3-phenyl-6-methyl-7-hydroxy-furo-(3,4-c)-pyridine This compound was obtained as described in example 17 but replacing, in step (iii), the phenyl bromide by p-[N-(α-methoxypyrrolidinyl)]-phenyl bromide. Yield: 73% of a white crystalline product melting at 189° C. (Tottoli), elemental analysis of which showed good correspondence with the formula $C_{25}H_{26}N_2O_3 \cdot HCl$. The compound was insoluble in water at room temperature.

EXAMPLE 24

1,3-dihydro-3,3-di-(p-fluorophenyl)-6-methyl-7-hydroxy-furo-(3,4-c)-pyridine

This compound was obtained as described in example 1 but replacing the methyl iodide by p-fluorophenyl bromide in steps (i) and (iii). Yield: 71% of a white crystalline product melting at 236°–239° C. (Tottoli), elemental analysis of which showed good correspondence with the formula $C_{20}H_{15}F_2NO_2$. The compound was insoluble in water at room temperature but soluble in dimethylsulphoxide.

EXAMPLE 25

1,3-dihydro-3-(α-furyl)-3-(p-methylthio-phenyl)-6-methyl-7-hydroxy-furo-(3,4-c)-pyridine This compound was obtained as described in example 13 but replacing the ethyl iodide, in step (iii), by p-thiomethylphenyl bromide. Yield 52% of a beige powder melting at 176° C. (Tottoli), elemental analysis of which showed good correspondence with the formula $C_{19}H_{17}NO_3S \cdot HCl$. The compound was slightly soluble in water at room temperature.

EXAMPLE 26

1,3-dihydro-3,3-di(α-furyl)-6-methyl-7-hydroxy-furo-(3,4-c)-pyridine

This compound was obtained as described in example 13 but replacing the ethyl iodide, in step (iii), by α-furyl bromide. Yield 56% of a beige powder melting at 184° C. (Tottoli), elemental analysis of which showed good correspondence with the formula $C_{16}H_{13}NO_4 \cdot HCl$. The compound was slightly soluble in water at room temperature.

EXAMPLE 27

1,3-dihydro-3-cyclohexyl-3-(2,3-dichlorophenyl)-6-methyl-7-hydroxy-furo-(3,4-c)-pyridine This compound was obtained as described in example 1 but replacing the methyl iodide by 2,3-dichlorophenyl bromide in step (i) and by cyclohexyl bromide in step (iii). Yield: 76% of a white crystalline product melting with decomposition at 195°–197° C. (Tottoli), elemental analysis of which showed good correspondence with the formula $C_{20}H_{21}Cl_2NO_2$. The compound was insoluble in water at room temperature but soluble in 0.1N HCl.

EXAMPLE 28

1,3-dihydro-3-cyclohexyl-3-(p-chlorophenyl)-6-methyl-7-hydroxy-furo-(3,4-c)-pyridine This compound was obtained as described in example 27 but replacing 2,3-dichlorophenyl bromide by p-chlorophenyl bromide in step (i). Yield: 79% of a white crystalline product melting at 205°–208° C. (Tottoli), elemental analysis of which showed good correspondence with the formula $C_{20}H_{22}ClNO_2$. The compound was insoluble in water at room temperature but soluble in 0.1N HCl.

EXAMPLE 29

1,3-dihydro-3-cyclohexyl-3-(p-fluorophenyl)-6-methyl-7-hydroxy-furo-(3,4-c)-pyridine This compound was obtained as described in example 28 but replacing p-chlorophenyl bromide by p-fluorophenyl bromide in step (i). Yield: 83% of a white crystalline product melting with decomposition at 208°–210° C. (Tottoli), elemental analysis of which showed good correspondence with the formula $C_{20}H_{22}FNO_2$. The compound was insoluble in water at room temperature but soluble in 0.1N HCl.

Example 30

1,3-dihydro-3,3-dicyclohexyl-6-methyl-7-hydroxy-furo-(3,4-c)-pyridine

This compound was obtained as described in example 1 by using cyclohexyl bromide in both steps. Yield: 69% of a white crystalline product melting with decomposition at 187°–190° C. (Tottoli), elemental analysis of which showed good correspondence with the formula $C_{20}H_{29}NO_2$. The compound was insoluble in water at room temperature but soluble in 0.1N HCl.

TOXICITY

The toxicity of the compounds according to the invention has been determined on rats and mice, by oral route. No LD 50 could be found for no death was noticed at the dose of 5 g/Kg for rats and of 2 g/Kg for mice.

A sub-acute toxicity study was undertaken on rats and dogs at the doses of 10,60 and 360 mg/Kg for six weeks by oral route: neither death was noticed nor any variation of the measurable factors.

PHARMACOLOGY

The interest of the compounds of the invention has been evidenced by various pharmacologic tests.

(1°) Study of the urinary elimination in the rat

This study has been conducted on Wistar male rats weighing 250-260 g.

Sixteen batches of each eight animals were used: one for control, one treated by tienilic acid as reference compound and fourteen batches by the compounds according to the invention, all animals of these fifteen batches at the same dose of 50 mg/kg/day.

The animals were treated for three days and placed in a metabolic cage fitted for the collection of urines; neither food nor drink was given during the treatment in order to avoid any contamination. The collected volumes of urine are measured after six hours and twenty four hours. After six hours, each animal receives 25 ml/kg of physiologic serum. On the fourth day, the animal receives a last treatment and blood is taken off at the retro orbital sinus under slight anaesthesia by diethyl ether. The results are reported in the table 1.

(2°) Action on blood pressure

This study was conducted on rats suffering from induced high blood pressure, by the method of GOLDBLATT in comparison with Indapamine. This method is no longer described, for it is well known and the study shows, at the same therapeutic doses, that the compounds of the invention have, on this test, the same action for the lowering of blood pressure on the rats.

(3°) Action on an experimental hyper lipemia on rabbit

This study has been conducted according to the method of C. B. AMMERMAN and Coll.; Am. J. PHYS. (1961) 200, 75–79.

In this method, the suppression of drink for five days, induces in the rabbit a higher hepatic bio-synthesis of cholesterol. Blood is taken off after the sixth day in the abdominal aorta for the dosage of total lipids, triglycerids, total cholesterol, HDL cholesterol (enzymatic method after electrophoresis on cellulose acetate).

The livers are taken off and weighted. In all the cases the administration was done directly in the oesophagus from the third to the fith days. This experimentation has been conducted simultaneously on 15 batches of each six animals, two control batches (normal control and control without food), one reference batch (animal without food but treated by tienilic acid) and the last twelve batches by twelve of the compounds of the invention. These thirteen last batches receive 50 mg/kg/day. The results are reported in table 2 wherein the letters A to F represent:

A: Weight of livers in g,
B: Total lipids in g/l,
C: Triglycerids in g/l,
D: Total cholesterol in g/l,
E: HDL cholesterol in g/l (two columns),
F: LDL cholesterol in g/l.

TABLE 1

| Administration per os of 50 mg/kg/day | Volumes (ml) | | |
|---|---|---|---|
| | 0–6 h | 6–24 h | 0–24 h |
| Control | 5.7 | 14.1 | 19.8 |
| Tienilic acid | 8.0 | 8.9 | 16.7 |
| EX. 1 | 10.2 | 10.6 | 20.8 |
| EX. 3 | 10.2 | 10.6 | 20.6 |
| EX. 4 | 10.4 | 10.9 | 20.7 |
| EX. 6 | 10.0 | 10.8 | 20.5 |
| EX. 8 | 10.1 | 10.7 | 20.5 |
| EX. 11 | 10.3 | 11.0 | 20.9 |
| EX. 12 | 10.1 | 10.8 | 20.3 |
| EX. 15 | 8.8 | 10.0 | 20.1 |
| EX. 17 | 10.1 | 10.8 | 21.0 |
| EX. 20 | 10.5 | 11.4 | 21.3 |
| EX. 21 | 10.2 | 10.9 | 20.8 |
| EX. 24 | 10.1 | 10.6 | 20.2 |
| EX. 28 | 9.8 | 10.9 | 20.4 |
| EX. 30 | 10.5 | 11.2 | 21.1 |

TABLE 2

| | Plasmatic values | | | | Cholesterol of the lipoproteins | | Total cholesterol |
|---|---|---|---|---|---|---|---|
| | A | B | C | D | E | F | E |
| Control | 3.52 | 5.18 | 1.69 | 0.83 | 0.18 | 0.29 | 4.73 |
| Control without food | 2.52 | 11.10 | 1.23 | 2.66 | 0.41 | 2.12 | 6.81 |
| Tienilic acid | 2.80 | 12.28 | 1.97 | 2.48 | 0.23 | 1.77 | 15.72 |
| EX. 1 | 2.63 | 11.05 | 1.48 | 2.51 | 0.31 | 1.70 | 8.01 |
| EX. 3 | 2.79 | 11.67 | 1.53 | 2.47 | 0.30 | 1.62 | 7.93 |
| EX. 6 | 2.72 | 11.44 | 1.57 | 2.50 | 0.24 | 1.65 | 8.17 |
| EX. 8 | 2.72 | 12.04 | 1.47 | 2.48 | 0.27 | 1.67 | 8.31 |
| EX. 11 | 2.65 | 11.56 | 1.61 | 2.50 | 0.28 | 1.67 | 7.79 |
| EX. 12 | 2.66 | 12.10 | 1.62 | 2.46 | 0.29 | 1.63 | 8.16 |
| EX. 15 | 2.77 | 11.86 | 1.44 | 2.49 | 0.25 | 1.66 | 8.19 |
| EX. 17 | 2.70 | 11.93 | 1.49 | 2.47 | 0.27 | 1.64 | 8.24 |
| EX. 20 | 2.69 | 11.79 | 1.44 | 2.51 | 0.26 | 1.64 | 8.12 |
| EX. 24 | 2.78 | 11.97 | 1.48 | 2.46 | 0.27 | 1.70 | 7.85 |
| EX. 28 | 2.62 | 11.46 | 1.48 | 2.45 | 0.23 | 1.64 | 8.22 |
| EX. 30 | 2.65 | 11.88 | 1.50 | 2.53 | 0.29 | 1.67 | 8.22 |

In conclusion of the various experimentations it can be noticed that the compounds of the invention have a regular diuretic action slightly better than the known diuretics of the same chemical family (thiazidic). In human therapy, they have also an action on the lowering of blood pressure which is rather common in diuretics but limited to the patients presenting an hypertension. An other important fact is a significative lowering of the lipid rates in blood: this is a highly favorable action, for the patients treated by diuretics are generally suffering also from arteriosclerosis or other circulary insufficiencies wherein the lowering of the lipid rates is highly desired. For this reason, the compounds of the invention may be considered as diuretics offering a better protection of the patient.

CLINICAL EXPERIMENTATION

A clinical experimentation has been conducted on 127 patients with compounds of examples 3, 4 and 5. Each patient was treated as follows: on days 1, 3, 5 and 7, administration (double blind route) of a single dose of 100 mg or 200 mg or 400 mg of the selected compound or an equivalent presentation of placebo at 10.00 a.m. after a complete urination. Urins were collected for the following 24 hours for determination of the diuresis. No treatment was given on days 2, 4 and 6.

The diuresis was increased by 130 to 164% at the dose of 100 mg, by 192 to 248% at the dose of 200 mg and 288 to 371% at the dose of 400 mg (percentages given by reference to the action of placebo) with a better tolerance than with the compounds of previous patent application referred to in page 2.

PRESENTATION

The preferred mode of administration includes tablets and gelatine capsules; for tablets the dosage units comprise 50 or 100 mg of active ingredient together with an appropriate carrier, such as, for instance, starch.

POSOLOGY

In human therapy it is generally advisable to administer 100 to 400 mg per diem for at least one week and, more generally, two or three weeks.

I claim:

1. A 1,3-dihydro-6-methyl-7-hydroxy-furo-(3,4-c)-pyridine derivative of the formula I

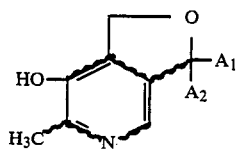

wherein $A_1$ is methyl and $A_2$ independently represents a straight chain saturated hydrocarbon group having from 1 to 5 carbon atoms or a straight chain unsaturated hydrocarbon group having from 2–5 carbon atoms, a thienyl or furyl group, a phenyl group or a cyclohexyl group, a phenylalkyl group or a phenylalkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms; or a therapeutically acceptable addition salt thereof.

2. A diuretic, hypotensive or hypolipidemic composition comprising an amount sufficient to be effective as a diuretic, hypotensive or hypolipidemic agent of a furo-(3,4-c)-pyridine derivative, or salt thereof as defined in claim 1, in admixture with a pharmaceutically acceptable diluent or carrier.

3. A method of reducing histamine level in a subject in need thereof comprising the administration of an anti-histaminically effective amount of a furo-(3,4-c)-pyridine derivative, or salt thereof, as defined in claim 1.

* * * * *

UNITED STATES PATENT AND TRADEMARK OFFICE
CERTIFICATE OF CORRECTION

PATENT NO. : 4,735,950
DATED : April 5, 1988
INVENTOR(S) : Andre Esanu

It is certified that error appears in the above-identified patent and that said Letters Patent are hereby corrected as shown below:

Column 1, line 6, after "This" insert --is--.

Column 1, lines 18-25 and Column 10, lines 52-60, delete the formula I shown and replace with the following formula I:

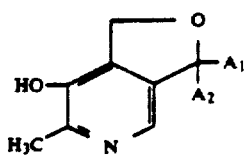

Column 1, lines 52-60 and Column 2, lines 5-13, delete the formula shown and replace with the following formula:

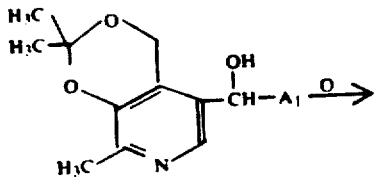

UNITED STATES PATENT AND TRADEMARK OFFICE
CERTIFICATE OF CORRECTION

PATENT NO. : 4,735,950
DATED : April 5, 1988
INVENTOR(S) : Andre Esanu

It is certified that error appears in the above—identified patent and that said Letters Patent are hereby corrected as shown below:

Column 2, lines 14-32, delete the formulas shown and replace with the following formulas:

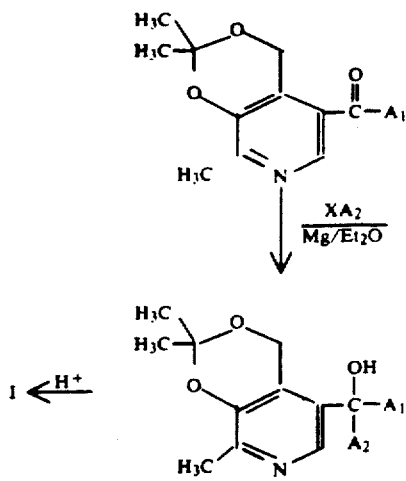

Signed and Sealed this

Twenty-seventh Day of December, 1988

Attest:

DONALD J. QUIGG

Attesting Officer

Commissioner of Patents and Trademarks